United States Patent [19]

Bagley et al.

[11] Patent Number: 4,900,738

[45] Date of Patent: Feb. 13, 1990

[54] N-HETEROCYCLIC-N-(4-PIPERIDYL)AMIDES AND PHARMACEUTICAL COMPOSITIONS AND THEIR USE AS ANALGESICS

[75] Inventors: Jerome R. Bagley, North Plainfield; H. Kenneth Spencer, Chatham, both of N.J.

[73] Assignee: BOC, Inc., New Providence, N.J.

[21] Appl. No.: 255,184

[22] Filed: Oct. 7, 1988

Related U.S. Application Data

[62] Division of Ser. No. 9,857, Feb. 2, 1987, Pat. No. 4,791,112.

[51] Int. Cl.⁴ .................... A61K 31/38; A61K 31/39; A61K 31/435; C07D 417/12
[52] U.S. Cl. .................................. 514/322; 514/321; 546/198; 546/199
[58] Field of Search ................ 546/198, 199; 514/321, 514/322

Primary Examiner—Mary C. Lee
Assistant Examiner—J. Richter
Attorney, Agent, or Firm—R. Hain Swope; Larry R. Cassett

[57] ABSTRACT

N-heterocyclic-4-piperidiyl-amides as analgesics and antagonists of opioids with respect to such undesirable side effects as respiratory depression.

Exemplary compounds have the formula

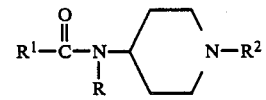

in which formula R is a heterocyclic group, and $R^1$ is a furanyl, thienyl, or lower alkoxy lower alkyl group, and $R^2$ is a lower alkyl phenyl group.

6 Claims, No Drawings

N-HETEROCYCLIC-N-(4-PIPERIDYL)AMIDES AND PHARMACEUTICAL COMPOSITIONS AND THEIR USE AS ANALGESICS

This is a divisional application of Ser. No. 07/009,857, filed 2/2/87, now U.S. Pat. No. 4,791,112.

The present invention relates to a class of N-heterocyclic-N-(4-piperidyl)-amides, and methods and compositions employing such compounds.

A number of patents disclose certain N-heterocyclic-N-(4-piperidyl)amides having therapeutic activity. For example, U.S. Pat. No. 4,546,105 to Effland et al. discloses pyrrolylamidopiperidines useful for the alleviation of pain. An article entitled "Synthesis and Analgesic Activity of Derivatives of Fentanyl" by Zhu You-cheng et al, printed in Acta Pharmaceutica Sinica, Vol. XVI, No. 3, March 1981 (pp 199–209) discloses various N-heterocyclic substituted amidopiperidines which possess morphine-like effects. Sigmar Grossmann Urich Moser and Ernest Mutschler, in Arch. Pharm. (Weinheim) 311, 1010–1015 (1978) disclose various pyridine analogues of fentanyl possessing analgesic activity. Frans Janssens et al., in Journal of Medicinal Chemistry, Vol. 28, No. 12, 1934–1947 (1985) disclose various N-heterocyclic-4-piperidinamides possessing antihistaminic properties.

BACKGROUND OF THE INVENTION

Antagonists in general possess the property of reversing a previously administered drug (the agonist). For example, the antagonist naloxone is well known for use in reversing selected properties of narcotic agonists. Antagonists of narcotics are believed to function by binding competitively to opioid receptors, thereby preventing occupation of the agonist. At least four types of opioid receptors have been identified in the central nervous system: mu, kappa, sigma, and delta. The affinity of a particular antagonist for each receptor may not be equal. However, antagonist compounds may act centrally or peripherally, at specific opiate receptors, through a non-specific analeptic mechanism, or through a neurotransmitter system. The full understanding of the complex affects of antagonists must await the elucidation of opioid physiology.

The prior art antagonist compound naloxone has gained widespread use in anesthesia for the purpose of antagonizing opioid induced respiratory depression and sedation, (Editorial, British Journal of Anesthesia, Vol. 57, No. 6, June 1985, pp 547–549). The use of naloxone in the presence of unwanted opioid effects has predominantly occurred in the immediate post operative period.

Recent information has supported the need for caution in the use of naloxone. This need for caution is based on reports of unwanted side effects of naloxone itself, including ventricular dysrhythmia, hypertension and pulmonary oedema following intravenous administration. Another disadvantage of naloxone as an antagonist is that naloxone tends to also reverse or antagonize the analgesic component of opioids.

There is therefore a need for a safe antagonist of opioid agonists which will selectively antagonize respiratory depression without the undesirable side effects of naloxone and which preferably does not antagonize the analgesia component of the opioid agonists.

SUMMARY OF THE INVENTION

Compounds of the present invention possess agonist-antagonist properties. The antagonist effect of the present compounds causes reversal of the actions of analgesics and anesthetics, for example, respiratory depression or cardiovascular depression. The preferred compounds of the present invention selectively reverse respiratory depression of narcotic or opiate analgesics without reversal of analgesia at that dose. Agonist-antagonists of this class of compounds are useful for post-operative pain control where respiratory depression but not analgesia must be reversed. Such compounds may be used pre-operatively or intra-operatively, including as a supplement to general anesthesia.

The agonist effect of the present compounds causes analgesia, decreased awareness of sensation and increases pain threshold. Preferred compounds of the present invention exhibit comparatively low cardio-respiratory adverse effects. At higher doses, compounds of the present invention produce sedation, loss of righting reflex, hypnosis and loss of consciousness.

It has now been found that very desirable agonist-antagonist properties are provided by compounds of the formula:

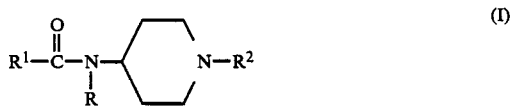
(I)

optically active isomeric forms thereof, and/or pharmaceutically acceptable acid addition salts thereof. In the Formula (I) above, R is a saturated or unsaturated heterocyclic ring system of 4 to 10 cyclic member atoms, including 1 to 3 nitrogen atoms, and 0 to 1 sulfur or oxygen atoms, said heterocyclic ring system either substituted or unsubstituted by lower alkyl, halogen, lower alkoxy, halogenated lower alkyl, lower alkylthio or combinations thereof; $R_1$ is a furanyl or thienyl group or a lower alkoxy lower alkyl group; and $R^2$ is a phenyl lower alkyl group.

A preferred class of compounds within the scope of the present invention are of the formula

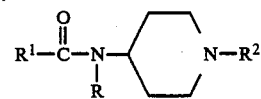

optically active isomeric forms thereof, and/or pharmaceutically acceptable acid addition salts thereof, in which formula: R is a substituent selected from the group consisting of pyrrolyl, piperidyl, pyrazyl, morpholyl, pyridyl, pyrimidyl, triazolyl, indazolyl, indolyl, quinolyl, benzoxazolyl, benzisoxazolyl, benzothiazolyl, benzisothiazolyl, or benzothiadiazolyl, all of which may be unsubstituted or substituted with halogen, lower alkyl or combinations thereof; $R^1$ is furanyl or thienyl, or a lower alkoxy alkyl of 2–6 carbon atoms; and $R^2$ is phenyl lower alkyl.

DETAILED DESCRIPTION OF THE INVENTION

As noted above, the compounds of the invention have the formula

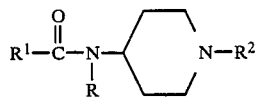

wherein R, $R^1$, and $R^2$, are as defined above. The compounds can be in the form of pharmaceutically acceptable acid addition salts, optionally active isomers, and/or cis/trans isomers thereof.

The group R in Formula I above is a heterocyclic ring system of 4 to 10 cyclic member atoms containing 1 to 3 nitrogen atoms and 0 to 1 oxygen or sulfur atoms. Preferred heterocyclic rings are selected from the group consisting of pyrrolyl, piperidyl, pyrazyl, morpholyl, pyridyl, pyrimidyl, triazolyl, indazolyl, indolyl, quinolyl, benzoxazolyl, benzisoxazolyl, benzothiazolyl, benzisothiazolyl, benzothiadiazolyl, the foregoing rings either unsubstituted or substituted, wherein the substituents are selected from the group consisting of halogen (preferably chlorine or fluorine), lower alkyl, lower alkoxy, halogenated lower alkyl, lower alkylthio or combinations thereof.

Suitable R groups include 1-pyrrolyl, 1,2,4-triazol-4-yl, 1-piperidyl, 4-morpholyl, 2-pyridyl, 4-methyl-2-pyridyl, 3-pyridyl, 4-pyridyl, 2-chloro-3-pyridyl, 2-chloro-5-pyridyl, 2-pyrimidyl, 2-pyrazyl, 2-chloro-4-pyrimidyl, 6-chloro-4-pyrimidyl, 4-chloro-6-pyrimidyl, 1,3-benzoxazol-2-yl, 1,3-benzothiazol-2-yl, 2,1,3-benzothia-diazol-4-yl, 1H-indazol-5-yl, 3-quinolyl, 1H-indol-5-yl, 2,1-benzisothiazol-3-yl, 1,2-benzisoxazol-3-yl, 5-chloro-1,2-benzisoxazol-3-yl, 1,2-benzisothiazol-3-yl. Preferred R groups are 4-methyl-2-pyridyl, 2-pyrazol, 2-chloro-3-pyridyl, and 2,1,3-benzothiadiazol-4-yl, 1-piperidyl, 2-pyrimidyl, 3-pyridyl, 2-chloro-4-pyrimidyl, and 4-chloro-6-primidyl.

The group $R^1$ in Formula I above is a furanyl or thienyl group, or a lower alkoxy lower alkyl. The furanyl or thienyl group is preferably attached to the carbonyl carbon at the 2 or 3 position of the ring. Example of suitable $R^1$ groups include methoxymethyl, ethoxymethyl, 1-propoxymethyl, 2-propoxymethyl, 1-butoxymethyl, 1-pentoxymethyl, 1-hexoxymethyl, 1-heptoxymethyl, 1-heptoxy-methyl, 1-methoxyethyl, 1-ethoxy-1-ethyl, 1-butoxy-1-ethyl, 2-furanyl, 3-furanyl, 2-thienyl, or 3-thienyl. A preferred $R^1$ group is 2-furanyl or 3-furanyl.

$R^2$ in Formula I above is a phenyl lower-alkyl. Suitable $R^2$ groups include 2-phenylethyl, 1-phenyl-2-propyl, and 2-phenyl-1-propyl.

By lower-alkyl or lower alkoxy groups, we mean branched or unbranched groups containing from 1 to 7 carbon atoms.

The compounds of the invention can exist in the form of the free base or the therapeutically or pharmaceutically acceptable acid addition salts by treatment with an appropriate acid, such as an inorganic acid, e.g., hydrochloric, hydrobromic, sulfuric, nitric, phosphoric acids and the like; or an organic acid such as acetic, trifluoroacetic, propionic, hydroxyacetic, methoxyacetic, benzoic, citric, oxalic, methanesulfonic, ethanesulfonic, benzenesulfonic, toluenesulfonic, succinic, tartaric, and the like acids. Preferred acid addition salts are the chloride, oxalate or citrate. These acid addition salts can be prepared by conventional methods, e.g., by treatment with the appropriate acid.

Compounds of the invention having at least one assymetric carbon atom can exist in optically active isomeric forms. For example, in compounds in which $R^2$ is a 2-phenyl-1-propyl or 1-phenyl-2-propyl group, etc., the carbon adjacent to the piperidinyl nitrogen is an assymetric carbon and such compounds can therefore exist in optical active isomeric (enantiomeric) forms. Such isomeric forms can be isolated from the racemic mixtures by techniques known to those skilled in the art.

The compounds of the invention, prepared as the free base, can be combined with a pharmaceutically acceptable carrier to provide a pharmaceutical composition. Suitable carriers for the free bases include propylene glycol-alcohol-water, isotonic water, sterile water for injection, USP, emulphor TM-alcohol-water, cremophor-EL TM or other carriers known to those skilled in the art.

The compounds of the invention prepared as the pharmaceutically acceptable acid addition salts can also be combined with a pharmaceutically acceptable carrier to provide a pharmaceutical composition. Suitable carriers for the acid addition salts may include an isotonic aqueous solution, or sterile water for injection, USP, alone or in combination with other solubilizing agents such as ethanol, propylene glycol, or other conventional solubilizing agents known to those skilled in the art. Of course, the carrier will vary depending upon the mode of administration desired for the pharmaceutical composition as is conventional in the art. A preferred carrier is an isotonic aqueous solution containing from 0.01 to 4.0 mg/ml of at least one of the compounds of this invention depending upon the pharmacology of the individual compounds being employed in the formulation.

The compounds of the invention can be administered to mammals, e.g., animals or humans, in amounts effective to provide the desired therapeutic effect. The compounds can be administered intravenously, intramuscularly or subcutaneously in the previously described carriers. These compounds may also be administered orally, sublingually, rectally, or transcutaneously with a suitable pharmaceutically acceptable carrier for that mode of administration as is conventional in the art.

As noted above, an effective amount of the compounds of the present invention is employed to obtain the desired therapeutic effect. Since the activity of the compounds and the depth of the desired therapeutic effect vary, the dosage level employed of the compound also varies. The actual dosage administered will be determined by such generally recognized factors as the body weight of the patient or the idiosyncrasies of the particular patient. Thus, the unit dosage for a particular patient (man) could be as low as 0.30 mg/Kg, which the practitioner may titrate to the desired effect.

The compounds of the present invention can be prepared by various methods. In general, the desired compounds of Formula I above can be prepared by reacting a compound of the formula

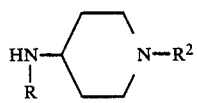

with a compound of the formula

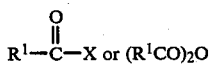

or by reacting a compound of the formula

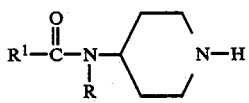

with a compound of the formula

R²X wherein R, R¹, R², R³ and R⁴ have the meanings given above and X represents halide or its reactive equivalent.

Several convenient routes for the preparation of the compounds of the invention begin with known piperidones as shown below:

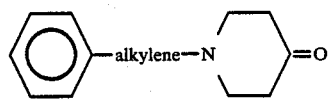

The compound 4-(2-phenylethyl)-piperidone can be prepared according to the procedure published by A. H. Becket, A. F. Casey and G. Kirk, *J. Med Pharm. Chem.*, Vol. 1, 37 (1959). The compound 4-benzyl-1-piperidone can be prepared in an analogous manner by the procedures described by C. R. Ganellin and R. G. Spickch, *J. Med. Chem.*, Vol. 8, 619 (1965) or P. M. Carabateas and L. Grumbach, *J. Med. Pharm. Chem.*, Vol. 5, 913(1962).

In one example of a process of the invention, 4-benzyl or 4-(2-phenylethyl)-piperidone may be reacted with a heterocyclic amine or a substituted heterocyclic amine and the resulting Schiff base may be reduced with, for example, sodium borohydride to give 1-benzyl or 1-(2-phenylethyl)-4-heterocyclic-aminopiperidine or the corresponding substituted heterocyclic compound if the substituted heterocyclic amine is used. See for example, Grossman, S. et al., Arch. Pharm. (Weinheim) 311, 1010 (1978). The following reaction scheme, wherein R represents a heterocyclic group according to the present invention, illustrates such a method:

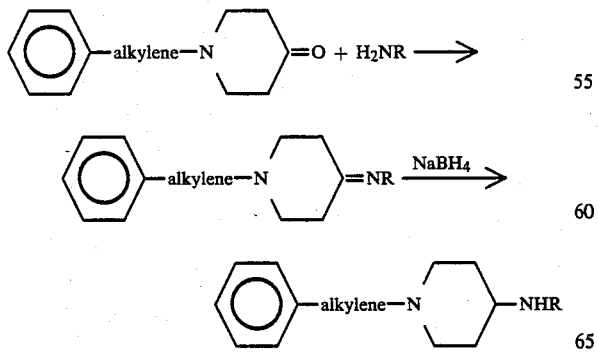

The latter compound can be reacted with the appropriate acid halide (e.g., R¹(COCl) or anhydride [(R¹CO)₂O] to introduce the appropriate R¹—CO— group into the amino nitrogen.

A second method for the preparation of the compounds of the invention utilizes the intermediate, 4-amino-1-R²-piperidine, for example, 4-amino-1-phenethyl piperidine. This method employs an aromatic nucleophilic substitution to obtain a secondary amino precursor for acylation. See, for example, Zhu, Y. et al, Acta Pharm Sinica, 16, 199 (1981). The following reaction scheme, where R represents a heterocyclic group according to the present invention, illustrates such a method:

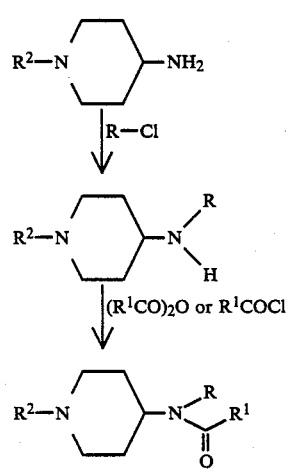

A third method for the preparation of compounds of the present invention also utilizes the intermediate 4-amino-1-R-piperidine, for example, 4-amino-1-phenylethyl piperidine. In this regard, see Langhein, et al., Offenlegungschrift, 234 1965 (1975); Chem. Abstr. 82, 156121W (1975).

This method involves reacting an oxo derivative of the heterocycle R with said intermediate to form a secondary amine which is reduced prior to acylation. The following reaction scheme illustrates such a method:

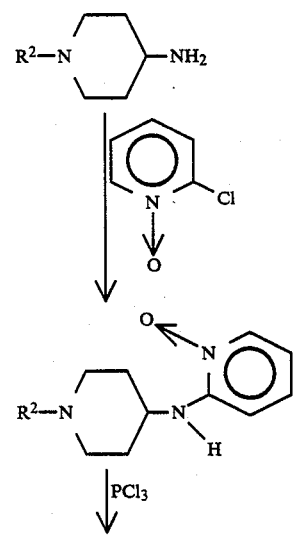

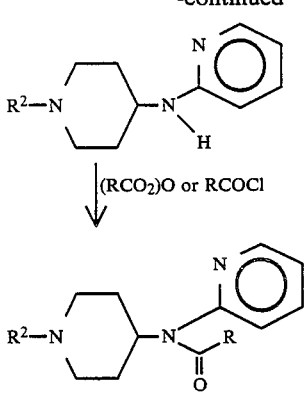

Finally, selective aromatic N-oxidation with meta-chloroperoxybenzoic acid of compounds of the present invention having pyridyl heterocyclic groups thereby yields desired N-oxide analogues.

The following examples are presented for purposes of demonstrating, but not limiting the compounds or compositions of this invention.

EXAMPLE I

An oxime intermediate was prepared as follows: Prior to use, N-(phenylethyl) piperidone was recrystallized from hexane in a 2000 ml beaker. 50 g (0.246 mol) of N-(phenylethyl) piperidone was dissolved in 200 ml of ethanol with necessary heat. This solution was added to a warm solution of 34.2 g (0.492 mol) of hydroxylamine hydrochloride and 200 ml of deionized water. An additional 500 ml of water was added to dissolve the phenylethylpiperidone oxime hydrochloride which began a precipitate. Solid NaHCO₃ (41.3 g, 0.492 mol) was added portionwise. The mixture was then heated to nearly boiling and set aside to cool to room temperature. Enough ice to fill a 1000 ml beaker was added and the mixture was stirred overnight. The solid product was filtered, washed with water (5×200 ml), and dried in vacuo. The crude oxime (52 g, 97%, mp 132°–133°) was sufficiently pure for use in the next reaction. An analytically pure sample (mp 132.5°–134.5°) of the following compound was obtained by recrystallization from 95% ethanol.

|   | Calcd | Found |
|---|-------|-------|
| C | 71.52 | 71.76 |
| H | 8.31  | 8.23  |
| N | 12.84 | 13.04 |

$$\text{NOH structure}$$

EXAMPLE II

The oxime of Example I was reduced as follows. Prior to use, tetrahydrofuran was dried by distillation from LiAlH₄ followed by storage over 3A molecular sievers. To a stirring suspension of 8.7 g (0.23 mol) of LiAlH₄ in 100 ml of dry tetrahydrofuran (THF), was added dropwise (at such a rate so as to maintain a brisk reflux) a solution of 50 g (0.23 mol) of oxime from Example I in 400 ml of THF. On completion of addition, the reaction mixture was heated under reflux overnight. The heating mantle was carefully replaced with a ice-water bath. Quenching, to liberate the basic product, consisted of successive additions of 8.7 ml of H₂O, 8.7 ml of 15% NaOH, and 26.1 ml of H₂O. The insoluble material was filtered, washed with THF (3×200 ml), and the combined filtrates concentrated in vacuo. The residual oil was dissolved in CH₂Cl₂ (300 ml), washed with water (2×100 ml), and dried over Na₂SO₄. Vacuum distillation of the crude oil, left after evaporation of solvent, gave a colorless product [35 g, 74%, bp 142° (0.10 mm Hg)]. The storage container was tightly capped and placed in a dessicator at this strongly basic amine forms salts of atmospheric carbon dioxide (H₂CO₃). An analytically pure sample of the following compound was obtained as the dihydrogen oxalate hemihydrate from i-PrOH-H₂O (mp 191°–192°).

|   | Calcd | Found |
|---|-------|-------|
| C | 51.90 | 51.58 |
| H | 6.41  | 6.21  |
| N | 7.12  | 7.11  |

EXAMPLE III

This example illustrates the preparation of an RX reagent, as generically defined supra, for reaction with the intermediate of Example II. The starting material 2-amino-4-picoline is commercially available from Aldrich. To an ice-chilled solution of 50 g (0.46 mol) of 2-amino-4-picoline, 250 ml of concentrated HCl and 150 ml of water was added, dropwise, a solution of NaNO₂ (32 g, 0.46 mol) in 150 ml of water (maintaining an internal temperature of between 0° and 3°). After addition of NaNO₂, the reaction mixture was stirred for 45 min. and then 120 ml of ice cold concentrated NH₄OH was added. A yellow suspension was extracted with chloroform (2×400 ml). This organic extract was washed with water (500 ml), brine (200 ml), and dried over Na₂SO₄. Concentration in vacuo left a green oil which was distilled (100°–110°, 30 mm Hg) to yield the product as a colorless oil (16 g, 27%) having the following structure:

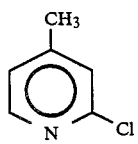

EXAMPLE IV

This example illustrates the further preparation of an RX reagent, as generically defined supra, for reaction with the intermediate of Example II. Under reflux, a mixture of 16 g (0.125 mol) of the product of Example III, 27 g (0.125 mol, 80%) of 3-chloroperbenzoic acid, and chloroform (250 ml) was stirred. After 4 hr. the mixture was cooled and partially concentrated to precipitate benzoic acid. The suspension was filtered and the filtrate washed with 6N NaOH, water, brine, and dried over $Na_2SO_4$. Purification by flash chromatography (400 g fine silica; $CHCl_3$—MeOH—$NH_3$, 100:1:0.1) yielded 6.2 g (35%) of the product having the following structure as a red oil which was found to be homogenous by TLC (Rf 0.30; $CHCl_3$—MeOH—$NH_3$, 95:5:0.5).

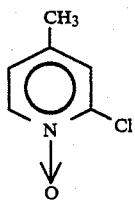

EXAMPLE V

This example illustrates the reaction of the intermediate of Example IV with the intermediate of Example II. A mixture of 6.2 g (43 mmol) of the product of Example IV, 9.2 g (45 mmol) of the product of Example II, 23 g anhydrous $Na_2CO_3$, 200 mg of KI, and 150 ml of 3-methyl-1-butanol was prepared. Under reflux the mixture was stirred for 48 hr. and then cooled and filtered. The filtrate was concentrated in vacuo. The residue was partitioned between 10% HCl (100 ml) and ether (100 ml). The acidic aqueous phase was alkalinized with 12N NaOH and the liberated free base was extracted with methylene chloride (2×100 ml). The organic extract was washed with water (100 ml), brine (50 ml), and dried over $Na_2SO_4$. Concentration in vacuo left a purple oil which was eluted through 650 g of fine silica with $CHCl_3$—MeOH—$NH_3$ (20:1:0.1) to yield the following product as a viscous, red oil (3.5 g, 26%) which was homogeneous by TLC (Rf 0.31; $CHCl_3$—MeOH—$NH_3$, 95:5:0:5).

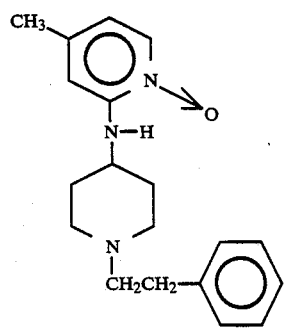

EXAMPLE VI

This example illustrates the reduction of the product of Example V. To an ice-chilled solution of 3.5 g (11.2 mmol) of the product of Example V in chloroform (80 ml) was added, dropwise, phosphorous trichloride (11.2 ml) while maintaining an internal temperature of 0°. After this, the reaction mixture was stirred under reflux for 2 hr, cooled, and poured into a 1000 ml beaker of ice. The acidic mixture was cautiously alkalinized with 20% NaOH. The liberated free base was extracted with methylene chloride (100 ml) and the organic extract washed with water (100 ml), brine (100 ml), and dried over $Na_2SO_4$. Initial purification by flash chromatography (120 g fine silica; $CHCl_3$—MeOH—$NH_3$; 25:1:01) yielded 2.4 g of a tan solid which required further chromatography (as previously), finally yielding the following product as a pale yellow solid (2.0 g, 61%).

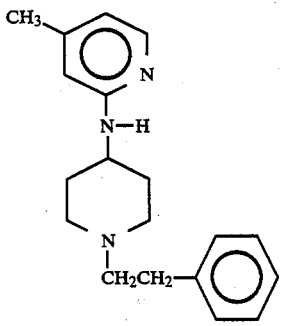

EXAMPLE VII

This example illustrates the conversion of the product of Example VI to a compound according to the present invention. To a stirring mixture of 0.94 g (3.2 mmol) of the product of Example VI, 1.0 ml of triethylamine and 8 ml of chloroform was added, with a disposable pipet, a solution of 0.38 ml of 2-furoyl chloride in 2 ml of chloroform. The mixing was mildly exothermic and after stirring at ambient temperature for 30 min, TLC analysis ($CHCl_3$—MeOH—$NH_3$, 95:5:0.5) indicated consumption of the starting material. The reaction mixture was partitioned between 10% HCl (50 ml) and ether (50 ml). The aqueous phase was further extracted with ether and then alkalinized with 12N NaOH. The liberated free base was extracted with methylene chloride (2×50 ml) and the organic extract washed with water (50 ml), brine (50 ml), and dried over $Na_2SO_4$. Purification by flash chromatography (60 g fine silica; $CHCl_3$—MeOH—$NH_3$, 30:1:0.1) gave a pale yellow solid (0.94 g, 75%). This was mixed with 217 mg of oxalic acid in hot isopropyl alcohol. A few drops of isopropyl ether induced the precipitation of a white powder (mp 197°-198°) which was further purified from isopropyl ether-isopropyl alcohol-methanol (to dissolve) yielding 787 mg of a white powder (mp 198°-199.5°) having the structure shown below.

|   | Calcd | Found |
|---|-------|-------|
| C | 65.12 | 64.80 |
| H | 6.10  | 6.10  |
| N | 8.76  | 8.76  |

-continued

| Calcd | Found |
|---|---|

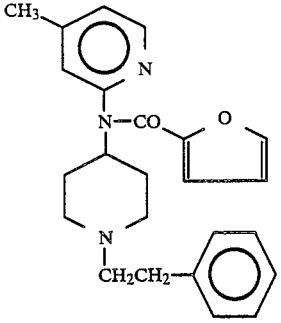

A second compound according to the present invention is prepared as described in the following two examples.

EXAMPLE VIII

An intermediate compound was prepared as follows. A mixture of 13 g (64 mmol) of the product of Example II above, 3.6 g (32 mmol) of chloropyrazine, and 2.0 g (32 mmol) of copper powder was stirred at 170°–180° for 6 hr. On cooling, a green mixture solidified. The solid was broken into chunks with a spatula and gradually churned into a thick soup in 10% HCl (100 ml). This was filtered of insolubles and the filtrate extracted with ether (50 ml). Alkalinization with 12N NaOH liberated the free base which was extracted with methylene chloride (2×50 ml). The organic extract was washed with water (50 ml), brine (50 ml), and dried over $Na_2SO_4$. The green solid left after evaporation of solvent was eluted through 600 g of fine silica. This required successive passages of $CHCl_3$—MeOH—$NH_3$ (4000 ml of 100:1:0.1, 1800 ml of 90:1:0.1, 1600 ml of 80:1:0.1, 4000 ml of 70:1:0.1) to yield 4.0 g (44%) of the following product as a beige solid.

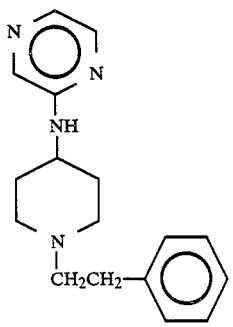

EXAMPLE IX

A compound according to the present invention was prepared from the intermediate of Example VIII as follows. To a stirring mixture of the product of Example VIII (1.5 g, 5.3 mmol), 1.5 ml of triethylamine, and 13 ml of chloroform was added, with a disposable pipet, 0.63 ml (6.4 mmol) of 2-furoyl chloride in 2 ml of chloroform. This was stirred under reflux for 5 hr, then cooled and concentrated in vacuo. The residue was partitioned between 10% HCl (50 ml) and ether (50 ml). The aqueous phase was alkalinized with 12N NaOH and extracted with methylene chloride (2×50 ml). The organic extract was washed with water (50 ml), brine (30 ml), and dried over $Na_2SO_4$. Purification by flash chromatography (55 g fine silica; $CHCl_3$—MeOH—$NH_3$, 30:1:0.1) gave a white solid (0.9 g, 45%). The hydrogen oxalate salt was initially precipitated from isopropyl alcohol and recrystallized from an isopropyl alcohol solution (containing the minimal amount of aqueous methanol required to dissolve salt) to finally yield 690 mg of a crude powder (mp 206°–207°) an oxalate salt of the compound having the following structure:

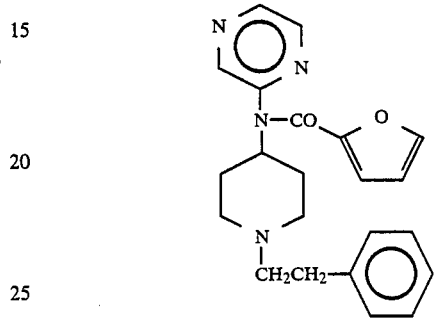

| | Calcd | Found |
|---|---|---|
| C | 61.79 | 62.17 |
| H | 5.62 | 5.61 |
| N | 12.01 | 12.28 |

The following three examples illustrate the preparation of another compound according to the present invention.

EXAMPLE X

An intermediate compound is prepared as follows. A mixture of N-phenethylpiperidone (17.4 g, 85.6 mmol), 4-amino-2,1,3-benzothiadiazole (15 g, 99.2 mmol), a few crystals of p-toluenesulfonic acid, and 170 ml of toluene was refluxed for 4 days. This time period is required for collection of the theoretical quantity of water-by-product (1.54 ml) in a Dean-Stark trap. The reaction mixture was cooled and concentrated in vacuo to give a reddish-brown oil which exhibits a strong Schoff base adsorption band (C=N, 1665 $cm^{-1}$) by infrared analysis. The structure of the compound was as follows:

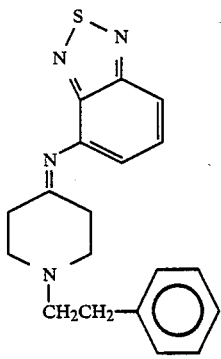

EXAMPLE XI

The intermediate of Example X was reduced as follows. To a solution of the product of Example X in 150 ml of methanol was added, portionwise, 3.7 g (98 mmol) of NaBH₄. The reaction mixture was heated under reflux for 2 hrs., cooled, and concentrated in vacuo. Water (100 ml) was added followed by extraction with toluene (200 ml). The organic extract was washed with water (2×100 ml) and dried over Na₂SO₄. Concentration in vacuo left 33.5 g of a dark brown oil which by infrared analysis was devoid of any Schiff base. This was purified by flash chromatography (800 g fine silica; hexane-ethyl acetate-triethylamine, 150:100:1) leaving a red oil which crystallized on standing at room-temperature. TLC analysis (hexane-ethyl acetate-triethylamine, 100:100:1) showed this to be the derived product with a trace of 4-amino-2,1,3-benzothiadiazole. A homogenous product was obtained by recrystallization from hexane, yielding 8.8 g (30%) of golden needles (mp 85°–88° C.). An analytical sample was obtained from isopropyl alcohol as the hydrogen oxalate salt (mp 189°–190° C.) having the following structure:

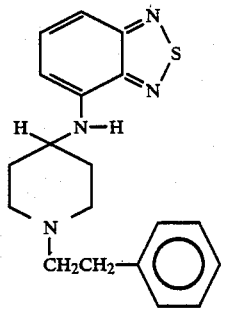

|   | Calcd | Found |
|---|-------|-------|
| C | 58.86 | 58.76 |
| H | 5.66  | 5.70  |
| N | 13.08 | 12.89 |

EXAMPLE XII

A compound according to the present invention was prepared from the intermediate of Example XI as follows. A mixture of the heteroaniline (1.0 g, 2.95 mmol), 3-furoyl chloride (0.77 g, 5.90 mmol), triethylamine (2 ml), and toluene (10 ml) was refluxed for 3 hr. The reaction mixture was concentrated in vacuo and partitioned between 10% HCl (50 ml) and ether (50 ml). Extraction of the aqueous acidic layer with additional ether was performed followed by liberation of free bases with 12N NaOH. These were extracted with CH₂Cl₂ (2×50 ml) and the combined organic extracts washed with water (50 ml), brine (30 ml), and dried over Na₂SO₄. The crude product left after evaporation of solvent was eluted through 80 g of fine silica with hexane-ethyl acetate-triethylamine (150:100:1; slow drip rate of 1 drop per 5 sec. overnight followed by air pressure the following morning) yielding 0.9 g of an amber gum. This was mixed with 187 mg of oxalic acid hot isopropyl alcohol. Precipitation of the salt was effected with addition of isopropyl ether. recrystallization from isopropyl ether-isopropyl alcohol-methanol-water yielded 673 mg of analytically pure product (mp. 191°–192° C.) having the following structure:

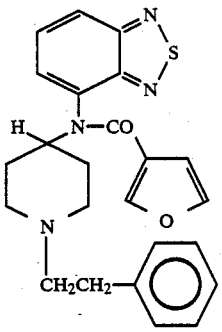

|   | Calcd | Found |
|---|-------|-------|
| C | 59.76 | 59.65 |
| H | 5.02  | 5.08  |
| N | 10.72 | 10.52 |

EXAMPLE XIII–XXII

Further examples of compounds within the scope of the present invention which may also be prepared by procedures analogous to those described above include:
N-(1-pyrrolyl)-N-[1-(2-phenylethyl)-4-piperidyl]-2-furamide.
N-(1,2,4-triazolyl-4-yl)-N-[1-(2-phenylethyl)-4-piperidyl]-3-furamide.
N-(2,1-benzisothiazol-3-yl)-N-[1-(2-phenylethyl)-4-piperidyl-3-furamide
N-(1,2-benzisoxazol-3-yl)-N-[1-(2-phenyethyl)-4-piperidyl]-3-furamide.
N-[5-chloro-1,2-benzisoxazol-3-yl]-N-[1-(2-phenylethyl)-4-piperidyl]-3-furamide.
N-[1,2-benzisothiazol-3-yl)-N-[1-(2-phenylethyl)-4-piperidyl)-2-furamide.
N-[6-chloro-1,2-benzisoxazol-3-yl]-N-[1-(2-phenylethyl)-4-piperidyl)-2-furamide.
N-(4-methylpyridin-2-yl)-N-[1-(2-phenyethyl)-4-piperidyl]-2-thienylamide.
N-(pyrazin-2-yl)-N-[1-(2-phenyethyl)-4-piperidyl]-2-thienylamide.
N-(2-chloropyridin-3-yl)-N-[1-(2-phenyethyl)-4-piperidyl]-3-thienylamide.

EXAMPLE XXIII

A number of compounds in accordance with the present invention were tested for their analgesic and reversal properties. Specifically, the acid addition oxalate salts of the compounds tested in accordance with the invention were dissolved in sterile water for injection, USP, to form a solution whose concentration varied from 0.00001 mg/ml to 5 mg/ml. The solution was administered intravenously in a mouse tail vain.

The ED₅₀ values were obtained from the mouse hot plate analgesia test (58° C.) described in Domer, Floyd R., *Animal Experiments in Pharmacological Analysis*, Charles C. Thomas, Springfield, 1971, p. 283 ff. The compounds listed in Table 1 below were tested by this procedure and found to have the analgesic activities listed in Table 1.

The reversal characteristics with respect to morphine were investigated in rabbits and categorized by an integer 0, 1, or 2, wherein the number 0 indicated no reversal of morphine effects, the number 1 indicated reversal of only morphine respiratory depression, and the number 2 indicated reversal of both respiratory depression and analgesia. The symbol NA indicates the compound was not active as an anesthetic or analgesic at less than 10 mg/kg.

without departing from the spirit and scope of the invention. All such modifications and variations are intended to be included within the scope of the invention as defined in the appended claims.

TABLE I

| COMPOUNDS | M.P. °C. | ANALGESIC ACTIVITY ED$_{50}$ MG/KG | REVERSAL CHARACTERISTICS |
|---|---|---|---|
| 1. N—(1-piperidyl)-N—[1-(2-phenyethyl)-4-piperidyl]-methoxy acetamide | 212–212.5 | 2.25 | 1 |
| 2. N—(1-piperidyl)-N—[1-(2-phenyethyl)-4-piperidyl]-2-furamide | 229–230 | 2.75 | 1 |
| 3. N—(4-morpholyl)-N—[1-(2-phenylethyl)-4-piperidyl]-methoxy-acetamide | 180–181 | NA | 0 |
| 4. N—(4-morpholyl)-N—[1-(2-phenylethyl)-4-piperidyl]-2-furamide | 203.5–205.5 | 2.25 | 1 |
| 5. N—(2-pyridyl)-N—[1-(2-phenyethyl)-4-piperidyl]-methoxyacetamide | 197–199 | 0.455 | 0 |
| 6. N—(2-pyridyl)-N—[1-(2-phenylethyl)-4-piperidyl]-2-furamide | 209–210.5 | 0.081 | 1 |
| 7. N—(2-pyridyl)-N—[1-(2-phenylethyl)-4-piperidyl]-3-furamide | 198.5–201 | 0.8 | 1 |
| 8. N—(3-pyridyl)-N—[1-(2-phenylethyl)-4-piperidyl]-2-thienamide | 208–209 | 2.5 | 2 |
| 9. N—(2-pyridyl)-N—[1-(2-phenylethyl)-4-piperidyl]-2-thienamide | 215–217.50 | 1.0 | 1 |
| 10. N—(4-methyl-pyridin-2-yl)-N—[1-(2-phenyethyl)-4-piperidyl]-2-furamide | 198–199 | NA | 2 |
| 11. N—(3-pyridyl)-N—[1-(2-phenylethyl)-4-piperidyl]-2-furamide | 194–194.5 | 1.5 | 1 |
| 12. N—(3-pyridyl)-N—[1-(2-phenylethyl)-4-piperidyl]-3-furamide | 191–192 | 0.69 | |
| 13. N—(2-chloro-pyridin-3-yl)-N—[1-(2-phenylethyl)-4-piperidyl]-methoxyacetamide | 149–151 | 3.9 | 0 |
| 14. N—(2-chloro-pyridin-3-yl)-N—[1-(2-phenylethyl)-4-piperidyl]-2-furamide | 177–179 | 5.2 | 2 |
| 15. N—(2-chloro-pyridin-3-yl)-N—[1-(2-phenylethyl)-4-piperidyl]-3-furamide | 118–123 | 7.5 | 1 |
| 16. N—(2-chloro-pyridin-5-yl)-N—[1-(2-phenylethyl)-4-piperidyl]-methoxyacetamide | 180–182 | NA | 1 |
| 17. N—(2-chloro-pyridin-5-yl)-N—[1-(2-phenylethyl)-4-piperidyl]-2-furamide | 213–214 | 2.8 | 1 |
| 18. N—(2-chloro-pyridin-5-yl)-N—[1-(2-phenylethyl)-4-piperidyl]-3-furamide | 191.5–192 | 7.5 | 1 |
| 19. N—(2-pyrimidyl)-N—(2-phenylethyl-4-piperidyl]-methoxyacetamide | 188–190 | 1.7 | 1 |
| 20. N—(2-pyrimidyl)-N—[1-(2-phenylethyl-4-piperidyl]-2-furamide | 211–212 | 10.0 | 2 |
| 21. N—(2-pyrimidyl)-N—[1-(2-phenylethyl-4-piperidyl]-3-furamide | 212–214.5 | 2.25 | 1 |
| 22. N—(2-pyrazyl)-N—[1-(2-phenylethyl-4-piperidyl]-2-furamide | 206–207 | 2.25 | 1 |
| 23. N—(2-pyrazyl)-N—[1-(2-phenylethyl-4-piperidyl]-3-furamide | 204.5–207.5 | 4.7 | 1 |
| 24. N—(2-chloro-pyrimidin-4-yl)-N—[1-(2-phenylethyl)-4-piperidyl]-2-furamide | 173–174.5 | NA | 1 |
| 25. N—(2-chloro-pyrimidin-4-yl)-N—[1-(2-phenylethyl)-4-piperidyl]-3-furamide | 177–178 | 2.25 | 1 |
| 26. N—(4-chloro-pyrimidin-6-yl)-N—[1-(2-phenylethyl)-4-piperidyl]-methoxyacetamide | 163.5–164 | NA | 1 |
| 27. N—(4-chloro-pyrimidin-6-yl)-N—[1-(2-phenylethyl)-4-piperidyl]-2-furamide | 193–195 | NA | 2 |
| 28. N—(4-chloro-pyrimidin-6-yl)-N—[1-(2-phenylethyl)-4-piperidyl]-3-furamide | 185–186.5 | NA | 1 |
| 29. N—(4-pyridyl)-N—[1-(2-phenylethyl)-4-piperidyl]-2-furamide | 181–183 | 1.7 | 2 |
| 30. N—(4-pyridyl)-N—[1-(2-phenylethyl)-4-piperidyl]-3-furamide | 192–195 | 2.75 | 2 |
| 31. N—(1,3-benzoxazol-2-yl)-N—[1-(2-phenylethyl)-4-piperidyl]-methoxyacetamide | 205–206.5 | 2.5 | 0 |
| 32. N—(1,3-benzoxazol-2-yl)-N—[1-(2-phenylethyl)-4-piperidyl]-2-furamide | 210.5–211.5 | 2.5 | 1 |
| 33. N—(1,3-benzoxazol-2-yl)-N—[1-(2-phenylethyl)-4-piperidyl]-3-furamide | 219–219.5 | NA | 1 |
| 34. N—(1,3-benzothiazol-2-yl)-N—[1-(2-phenylethyl)-4-piperidyl]-methoxyacetamide | 220–222 | 1.95 | 0 |
| 35. N—(1,3-benzothiazol-2-yl)-N—[1-(2-phenylethyl)-4-piperidyl]-2-furamide | 226.5–227 | | 1 |
| 36. N—(1,3-benzothiazol-2-yl)-N—[1-(2-phenylethyl)-4-piperidyl]-3-furamide | 232–232.5 | NA | 1 |
| 37. N—(1H-indol-5-yl)-N—[1-(2-phenylethyl)-4-piperidyl]-methoxy-acetamide | 139–180 | 10.0 | 0 |
| 38. N—(1H-indol-5-yl)-N—[1-(2-phenylethyl)-4-piperidyl]-methoxy-acetamide | 150–152 | NA | 0 |
| 39. N—(2,1,3-benzothiadiazol-4-yl)-N—[1-(2-phenylethyl)-4-piperidyl]-methoxyacetamide | 176–178 | 1.85 | 0 |
| 40. N—(2,1,3-benzothiadiazol-4-yl)-N—[1-(2-phenylethyl)-4-piperidyl[-2-furamide | 142–145 | 3.5 | 2 |
| 41. N—(2,1,3-benzothiadiazol-4-yl)-N—[1-(2-phenylethyl)-4-piperidyl]-3-furamide | 191–192 | 2.25 | 1 |
| 42. N—(3-quinolyl)-N—[1-(2-phenylethyl)-4-piperidyl]-2-furamide | 171.5–175 | 0.78 | 1 |
| 43. N—(2-pyrazyl)-N—[1-(2-phenethyl)-4-piperidyl]-2-thienamide | 228–230 | 3.5 | 1 |

It will be understood that the embodiments described herein are merely exemplary and that a person skilled in the art may make many variations and modifications

We claim:
1. A compound having the formula

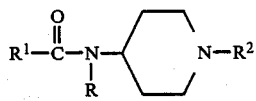

optically active isomeric forms, or pharmaceutically acceptable acid addition salts thereof, in which formula: R is selected from the group consisting of benzoxazolyl, benzisoxazolyl, benzothiazolyl, benzisothiazolyl and benzothiadazolyl groups which may be unsubstituted or substituted wherein the substituents are selected from the group consisting of halogen, lower alkyl, lower alkoxy, halogenated lower alkyl, lower alkylthio or combinations thereof; $R^1$ is furanyl or thienyl or a lower alkoxy lower alkyl; and $R^2$ is a phenyl lower alkyl.

2. A compound according to claim 1, which is N-(2,1,3-benzothiadiazol-4-yl)-N-[1-(2-phenylethyl)-4-piperidyl]-3-furamide.

3. A narocotic antagonistic or analgesic composition comprising a non-toxic pharmaceutically acceptable carrier and therapeutically effective amount of a compound of the formula

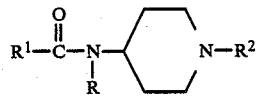

optically active isomeric forms, or pharmaceutically acceptable acid addition salts thereof, in which formula: R is selected from the group consisting of benzoxazolyl, benzisoxazolyl, benzothiazolyl, benzisothiazolyl and benzothiadiazolyl groups which may be unsubstituted or substituted wherein the substituents are selected from the group consisting of halogen, lower alkyl, lower alkoxy, halogenated lower alkyl, lower alkylthio or combinations thereof; $R^1$ is furanyl or thienyl or a lower alkoxy lower alkyl; and $R^2$ is a phenyl lower alkyl.

4. A composition according to claim 3, which comprises N-(2,1,3-benzothiadiazol-4-yl)-N-[1-(2-phenylethyl)-4-piperidyl]-3-furamide as the active ingredient.

5. A method for producing selective reversal of the actions of opiate analgesics, including respiratory depression, in a mammal comprising administering to such mammal an antagonistically effective amount of a compound of the formula

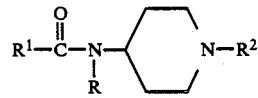

optically active isomeric forms, or pharmaceutically acceptable acid addition salts thereof, in which formula: R is selected from the group consisting of benzoxazolyl, benzisoxazolyl, benzothiazolyl, benzisothiazolyl and benzothiadiazolyl groups which may be unsubstituted or substituted wherein the substituents are selected from the group consisting of halogen, lower alkyl, lower alkoxy, halogenated lower alkyl, lower alkylthio or combinations thereof; $R^1$ is furanyl or thienyl or a lower alkoxy lower alkyl; and $R^2$ is a phenyl lower alkyl.

6. A method according to claim 5, which comprises administering N-(2,1,3-benzothiadiazol-4-yl)-N-[1-(2-phenylethyl)-4-piperidyl]-3-furamide.

* * * * *